(12) United States Patent
Wei et al.

(10) Patent No.: US 8,084,095 B2
(45) Date of Patent: Dec. 27, 2011

(54) CERAMIC/STRUCTURAL PROTEIN COMPOSITES AND METHOD OF PREPARATION THEREOF

(75) Inventors: Mei Wei, Coventry, CT (US); Haibo Qu, Secane, PA (US)

(73) Assignee: The University of Connecticut, Farmington, CT (US)

( * ) Notice: Subject to any disclaimer, the term of this patent is extended or adjusted under 35 U.S.C. 154(b) by 536 days.

(21) Appl. No.: 12/265,979

(22) Filed: Nov. 6, 2008

(65) Prior Publication Data

US 2009/0130456 A1    May 21, 2009

Related U.S. Application Data

(60) Provisional application No. 60/985,679, filed on Nov. 6, 2007.

(51) Int. Cl.
*B05D 3/02* (2006.01)
(52) U.S. Cl. .................. 427/372.2; 427/384; 427/385.5; 427/388.1; 427/388.4; 427/393.5; 427/393.6
(58) Field of Classification Search .................. None
See application file for complete search history.

(56) References Cited

U.S. PATENT DOCUMENTS

| | | | |
|---|---|---|---|
| 4,888,366 A | 12/1989 | Chu et al. | |
| 6,136,369 A | 10/2000 | Leitao et al. | |
| 6,187,047 B1 | 2/2001 | Kwan et al. | |
| 6,887,488 B2 | 5/2005 | Cui et al. | |
| 7,087,086 B2 | 8/2006 | Li et al. | |
| 7,153,938 B2 | 12/2006 | Kikuchi et al. | |
| 7,879,093 B2 * | 2/2011 | Wei et al. .................. | 623/11.11 |
| 2002/0018797 A1 | 2/2002 | Cui et al. | |
| 2002/0018798 A1 | 2/2002 | Sewing et al. | |
| 2006/0204491 A1 | 9/2006 | Kakubo et al. | |
| 2006/0216494 A1 | 9/2006 | Furedi-Milhofer et al. | |
| 2007/0184299 A1 | 8/2007 | Wei et al. | |
| 2007/0255422 A1 * | 11/2007 | Wei et al. .................. | 623/23.51 |

FOREIGN PATENT DOCUMENTS

| | | | |
|---|---|---|---|
| EP | 1566186 A1 | 8/2005 | |
| WO | 2004024201 A2 | 3/2004 | |

OTHER PUBLICATIONS

Abstract and text of Gross et al, Journal of Biological Chemistry, 233, pp. 355-360, 1958.*
Qu et al., Synthesis of Dense Collagen/Apatite Composites Using a Biomimetic Method, Journal of the American Ceramic Society, vol. 91 Issue 10, pp. 3211-3215, Published Online: Aug. 26, 2008.
Qu and Wei, The Effect of Temperature and Initial pH on Biomimetic Apatite Coating, Journal of Biomedical Materials Research: 87B, 204-212 (2008).
Chen et al., Composite Coating of Bonelike Apatite Particles and Collagen Fibers on Poly L-Lactic Acid Formed Through an Accelerated Biomimetic Coprecipitation Process, 315-322, 2006.
Yanli et al., Formation of bonelike apatite-collagen composite coating on the surface of NiTi shape memory alloy, Scripta Materialia 54 (2006) 89-92.

(Continued)

*Primary Examiner* — Erma Cameron
(74) *Attorney, Agent, or Firm* — Cantor Colburn LLP

(57) ABSTRACT

Ceramic/structural protein composites and methods of preparation are disclosed, including coatings and films. Ceramic/structural protein coatings can be fabricated on the surface of substrates, including the surface of implantable medical devices.

9 Claims, 5 Drawing Sheets

OTHER PUBLICATIONS

Fan et al., A composite coating by electrolysis-induced collagen self-assembly and calcium phosphate mineralization, Biomaterials 26 (2005) 1623-1632.

Chen et al., PLLA scaffolds with biomimetic apatite coating and biomimetic apatite/collagen composite coating to enhance osteoblast-like cells attachment and activity, Surface & Coatings Technology 201 (2006) 575-580.

Gross et al., The Heat Precipitation of Collagen from Neutral Salt Solutions: Some Rate-Regulating Factors, The Journal of Biological Chemistry, vol. 233, No. 2, 355-360, Jan. 16, 1958.

Qu et al., Improvement of Bonding Strength Between Biomimetic Apatite Coating and Substrates, Part B: Applied Biomaterials: vol. 84B Issue 2, pp. 436-443 2007.

Qu et al., The Effect of Initial pH on Morphology of Biomimetic Apatite Coating, Key Engineering Materials vols. 330-332 (2007), pp. 757-760.

Kim et al., Bonding strength of bonelike apatite layer to Ti metal substrate, Journal of Biomedical Materials Research 1997, 38(2): 121-127.

Zhang et al., Hierarchical Self-Assembly of Nano-Fibrils in Mineralized Collagen, Chem. Mater. 2003, 15, 3221.

Barrere et al., Nucleation of biomimetic Ca-P coatings on Ti6A14V from a SBF × 5 solution: influence of magnesium, Biomaterials 23 (2002) 2211-2220.

Barrere et al., Influence of ionic strength and carbonate on the Ca-P coating formation from SBF×5 solution, Biomaterials 23 (2002) 1921-1930.

U.S. Appl. No. 11/619,659, filed Jan. 4, 2007, US 2007/0184299.

U.S. Appl. No. 12/265,956, filed Nov. 6, 2008, US 2009/0130168.

International Search Report; International Application No. PCT/US2008/082616; International Filing Date Jun. 11, 2008; 7 pages.

Written Opinion of the International Searching Authority; International Search Report; International Application No. PCT/US2008/082616; International Filing Date Jun. 11, 2008; 8 pages.

Chen et al., Biomimetic coating of apatite/collagen composite on Poly L-lactic Acid facilities cell seeding. Conf. Proc. IEEE Eng. Med. Biol. Soc. 2005, vol. 4, pp. 4087-4090, Abstract, 1 page.

International Searching Authority, International Search Report, PCT/US2008/082586, Date of Mailing: Jul. 6, 2009, 7 pages.

International Searching Authority, Written Opnion, PCT/US2008/082586, Date of Mailing: Jul. 6, 2009, 4 pages.

Yu et al., "Incorporation of bovine serum albumin into biomimetic coatings on titanium with high loading efficacy and its release behavior", J. Mater. Sci: Mater. Med. 20, 2008, pp. 287-294.

* cited by examiner

100μm

100μm

100μm 200 nm 5 nm

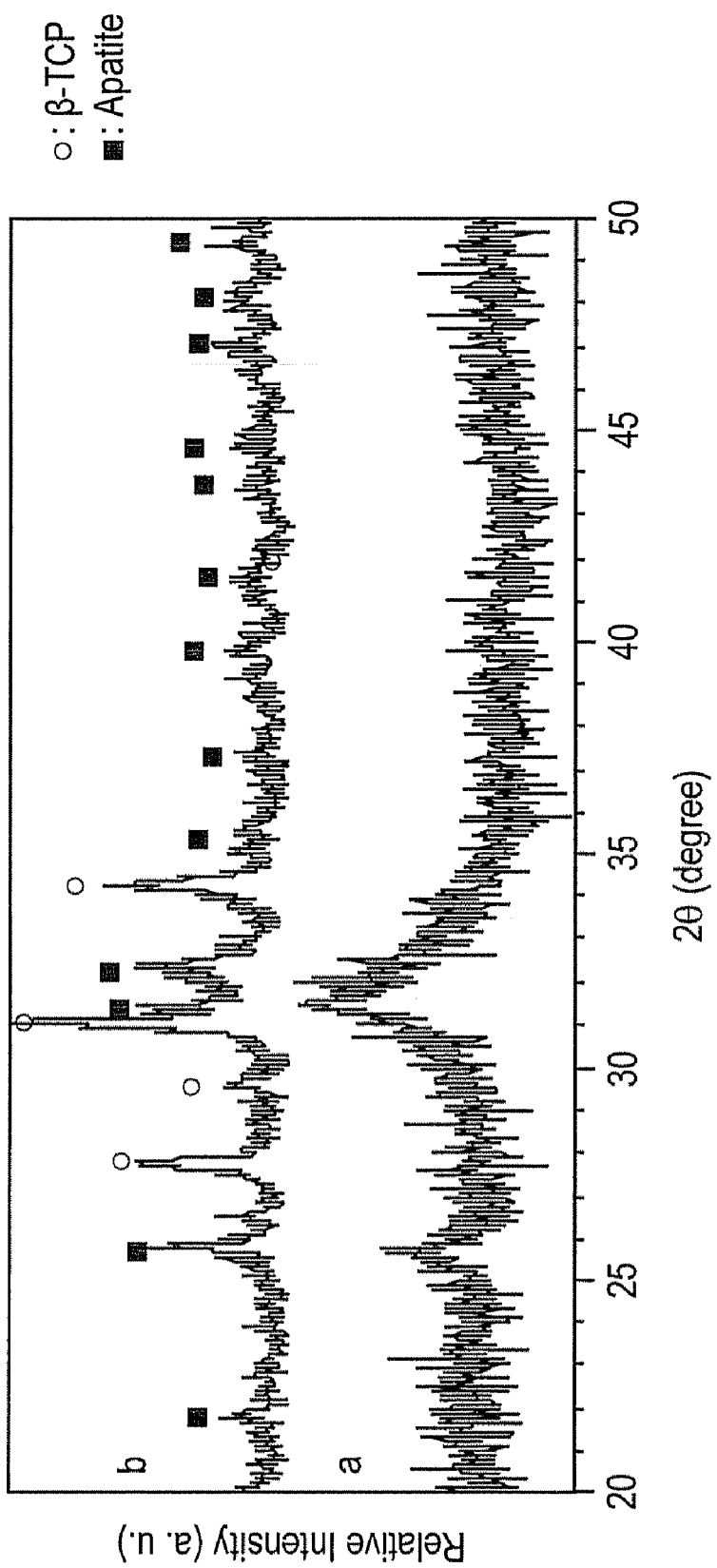

100nm

100nm

CERAMIC/STRUCTURAL PROTEIN COMPOSITES AND METHOD OF PREPARATION THEREOF

CROSS REFERENCE TO RELATED APPLICATION

This application claims the benefit of U.S. Provisional Application Ser. No. 60/985,679 filed Nov. 6, 2007, which is hereby incorporated by reference in its entirety.

STATEMENT REGARDING FEDERALLY SPONSORED RESEARCH

The U.S. Government has certain rights in this invention pursuant to Grant No. DMI 0500269 awarded by the National Science Foundation.

BACKGROUND OF INVENTION

Implantable medical devices, such as orthopedic and dental prostheses, can be made more permanent if the interface between the existing bone and the device contains some natural bone growth to knit the two components together. Such ingrowth has advantages over the use of bone cement, both in terms of stability and permanency.

"Bioactive" coatings on implantable medical devices allow for the ingrowth of natural bone into and around the device, forming chemical bonds between the device and natural bone. Bone is composed of substituted apatite crystals in an abundant collagen network. Type I collagen is the major protein of bone tissue, making up about thirty percent of the weight of bone. It has been shown that apatite crystals can grow and bond to collagen fibrils, and prepared apatite/collagen composites have been shown to promote direct bone apposition. However, there are drawbacks to these composites.

Electrophoresis has been used to prepare a bioactive apatite/collagen composite coating on a substrate. However, this method results in a relatively low bonding strength at the interface between the coating and the substrate.

Other groups have synthesized apatite/collagen composite coatings by the biomimetic method using simulated body fluid ("SBF"). The reported biomimetic methods took three days to obtain an apatite/collagen composite coating. The resulting coating contained collagen in colloidal/elliptical particles having sizes over two micrometers. Using a high saturated SBF solution (concentrated by a factor of five) containing collagen results in an inhomogeneous apatite/collagen composite coating which is unlike natural bone's ultra-structure at the nano-level. Under these conditions, the collagen fibers in the composite coating randomly overlapped and submicrometer apatite particles (200-600 nm) were attached on the collagen fibers.

Soluble collagen spontaneously forms into gel in neutral salt solutions within less than fours hours at physiological temperature (37° C.), while most of the apatite coating starts to deposit on substrate after fours hours under physiological conditions. As a result under traditional conditions in the biomimetic process, most of the collagen gelates and floats on the surface of the SBF solution or deposits on the surface of the substrate before the apatite precipitates. In the concentrated SBF case, apatite deposits on the surface of the collagen coating to form a laminated structure, and not a uniformly mixed composite. In both cases, only a small proportion of collagen is incorporated into the apatite coating and forms the nano-level apatite/collagen composite coating.

There remains a need in the art for improved bioactive composite coatings in addition to processes to prepare the composite coatings.

BRIEF DESCRIPTION OF THE INVENTION

In one embodiment, a method of coating a substrate comprises exposing a portion of a substrate to an aqueous system at a temperature of about 20° C. to about 80° C. to form a ceramic coating on a surface of the substrate; wherein the aqueous system comprises a structural protein, a gelation inhibitor agent, a weak acid, water, $Ca^{2+}$, $HPO_4^{2-}$, a buffer system, and optionally one or more of $Mg^{2+}$, $Na^+$, $K^+$, $Cl^-$, $SO_4^{2-}$; or $HCO_3^-$; and wherein the aqueous system has an initial pH of about 5.0 to about 8.0.

In another embodiment, a method of forming a film comprises forming an aqueous system comprising a structural protein, a gelation inhibitor agent, a weak acid, water, $Ca^{2+}$, $HPO_4^{2-}$, a buffer system, and optionally one or more of $Mg^{2+}$, $Na^+$, $K^+$, $Cl^-$, $SO_4^{2-}$; or $HCO_3^-$; wherein the aqueous system has an initial pH of about 5.0 to about 8.0; placing the aqueous system in container allowing for an air-aqueous system interface; sealing the container; and allowing a ceramic/structural protein film form at the air-aqueous system interface at a temperature of about 20° C. to about 80° C.

In another embodiment, a device comprises, i) a coated substrate prepared by the process comprising exposing a portion of a substrate to an aqueous system at a temperature of about 20° C. to about 80° C. to form a ceramic coating on a surface of the substrate; wherein the aqueous system comprises a structural protein, a gelation inhibitor agent, a weak acid having a pKa of about 3.0 to about 5.5, water, $Ca^{2+}$, $HPO_4^{2-}$, a buffer system, and optionally one or more of $Mg^{2+}$, $Na^+$, $K^+$, $Cl^-$, $SO_4^{2-}$; or $HCO_3^-$; and wherein the aqueous system has an initial pH of about 5.0 to about 8.0; or ii) a film prepared by the process comprising forming an aqueous system comprising a structural protein, a gelation inhibitor agent, a weak acid having a pKa of about 3.0 to about 5.5, water, $Ca^{2+}$, $HPO_4^{2-}$, a buffer system, and optionally one or more of $Mg^{2+}$, $Na^+$, $K^+$, $Cl^-$, $SO_4^{2-}$; or $HCO_3^-$; wherein the aqueous system has an initial pH of about 5.0 to about 8.0; placing the aqueous system in container allowing for an air-aqueous system interface; sealing the container; and allowing a ceramic/structural protein film form at the air-aqueous system interface at a temperature of about 20° C. to about 80° C.

Also disclosed herein are coatings and films prepared by the processes, as well as uses for the coatings and films.

BRIEF DESCRIPTION OF DRAWINGS

FIG. 4 XRD patterns of composite (a) before and (b) after TGA test.

DETAILED DESCRIPTION

Figure 1A:
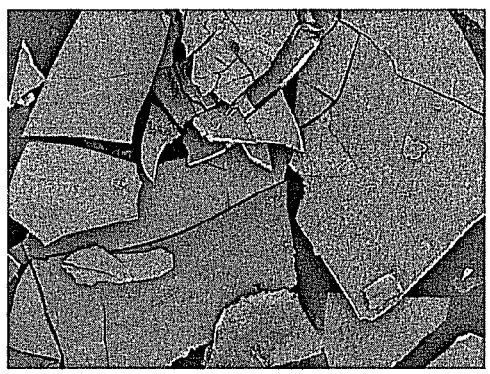
FIG. 1a FESEM image of apatite/collagen composite film surface morphology at a low magnification.

Disclosed herein are methods of forming ceramic/structural protein composite films and coatings; films and coatings prepared therefrom; and articles prepared therefrom.

The method described herein allows for a mild and convenient approach to form a ceramic/structural protein composite coating, specifically apatite/collagen composite coating on the surface of a variety of substrates. The method involves immersing a substrate or portion of a substrate into a coating aqueous system under controlled conditions of e.g., temperature, pH, ion concentration, and/or buffer to result in the formation of a ceramic/structural protein coating on the substrate surface. When used in implantable medical device applications, the apatite/collagen coating allows for bone ingrowth into the coating surface to form a strong bond between the substrate and existing bone.

With the disclosed method, a controllable collagen content dense apatite/collagen composite coating can be formed within twenty-four hours using a biomimetic method. The biomimetic method results in nano-structured, carbonated apatite and collagen composite that is chemically bonded to a substrate through the process of immersing the substrate in a coating aqueous system containing calcium, phosphate, structural protein gelation inhibitor agent (e.g., urea can prevent or inhibit collagen gelation) and a structural protein, specifically collagen. Other ions, such as sodium, potassium, magnesium, chloride, sulfate, and silicate, may optionally be present in the solution along with a buffer system.

In one embodiment, a method of coating a substrate with a structural protein composite coating comprises exposing at least a portion of a substrate to a coating aqueous system at a temperature of about 20° C. to about 80° C. to form a composite coating on a surface of the substrate; wherein the coating aqueous system comprises structural protein, water, $Ca^{2+}$, $HPO_4^{2-}$, a weak acid (e.g. acetic acid, and the like), a gelation inhibitor agent (e.g. urea, and the like), and a buffer system; and optionally one or more of the following ions: $Mg^{2+}$, $Na^+$, $K^+$, $Cl^-$, $SO_4^{2-}$, $HCO_3^-$; and wherein the coating aqueous system has an initial pH of about 50 to about 8.0. By varying the structural protein content in the coating aqueous system, the resulting ratio of ceramic/structural protein in the coating can be controlled.

The coating aqueous system generally comprises the following inorganic ions: $Ca^{2+}$ and $HPO_4^{2-}$, and optionally one or more of the following ions: $Mg^{2+}$, $Na^+$, $K^+$, $Cl^-$, $SO_4^{2-}$, and $HCO_3^-$. The coating aqueous system can be prepared by dissolving in an aqueous solvent salts that when disassociated will result in the particular ions $Ca^{2+}$, $Mg^{2+}$, $Na^+$, $K^+$, $Cl^-$, $SO_4^{2-}$, $HPO_4^{2-}$ and $HCO_3^-$. The aqueous solvent can be deionized and purified water. Exemplary salts include those that result in an aqueous solution of the desired ions, for example, alkali metal halides, alkaline earth metal halides, alkali metal hydrogen carbonates, alkali metal phosphates, and alkali metal sulfates. Exemplary salts include, NaCl, KCl, $K_2HPO_4$, $MgCl_2$, $Na_2SO_4$, $CaCl_2$ and $NaHCO_3$.

The particular concentrations of each of the above-described ions initially present in the coating aqueous system can be as follows:

$Ca^{2+}$ at about 2.5 to about 15.0 mM, specifically about 4.0 to about 12.0, and more specifically about 8.0 to about 10.0 mM;

$Mg^{2+}$ at about 0 to about 5.0 mM, specifically about 0.5 to about 4.5 mM, and more specifically about 1.5 to about 3.0 mM;

$Na^+$ at about 0 to about 300.0 mM, specifically about 50.0 to about 200.0 mM, and more specifically about 100.0 to about 150.0 mM;

$K^+$ at about 0 to about 20.0 mM, specifically about 2.0 to about 15.0 mM, and more specifically about 7.0 to about 10.0 mM;

$Cl^-$ at about 0 to about 350.0 mM, specifically about 50.0 to about 200.0 mM, and more specifically about 120.0 to about 150.0 mM;

$SO_4^{2-}$ at about 0 to about 2.0 mM, specifically about 0.1 to about 1.0 mM, and more specifically about 0.2 to about 0.5 mM;

$HPO_4^{2-}$ at about 1.0 to about 10.0 mM, specifically about 3.0 to about 8.0 mM, and more specifically about 5.0 to about 7.5 mM; and $HCO_3^-$ at about 0 to about 100.0 mM, specifically about 5.0 to about 50.0 mM, and more specifically about 20.0 to about 40.0 mM.

An additional component present in the coating aqueous system is a buffer system. The buffer system can contain HEPES (4-(2-hydroxyethyl)-1-piperazineethanesulfonic acid or N-2-hydroxyethylpiperazine-N'-2-ethanesulfonic acid; Molecular formula: $C_8H_{17}N_2SO_3$; CAS No: 7365-45-9) and an alkali metal hydrogen carbonate (e.g. $NaHCO_3$, KHCO3, etc.) which are added to the aqueous system in amounts to substantially stabilize the aqueous system. The concentration of HEPES present in the aqueous system can be at about 5.0 grams per liter (g/L) to about 80.0 g/L, specifically about 10.0 g/L to about 60.0 g/L, and more specifically about 12.0 g/L to about 48.0 g/L.

Additional buffer systems may include tris-hydroxymethyl aminomethane (TRIS), HEPES salts, piperazine-1,4-bis(2-ethanesulfonic acid) (PIPES), PIPES salts, combinations of the foregoing with an alkali metal carbonate, and combinations thereof.

The coating aqueous system may optionally contain additional ionic components such as silicate, strontium, zinc, silver, fluoride, combinations thereof, and the like.

The weak acid present in the aqueous system can be any acid with a pKa of about 3.0 to about 5.5, specifically about 4.5 to about 5.0. Exemplary acids include organic acids, specifically alkyl carboxylic acids such as acetic acid, propionic acid, and the like.

The gelation inhibitor agent is provided in the coating aqueous system to control the deposition of structural protein (e.g., collagen) such that it coincides with ceramic (e.g., apatite) formation. For example, hydrogen bonds between the hydroxyl groups of hydroxyproline and the keto group of the peptide links in the collagen backbone play a major role during collagen gelation. To decrease the rate of collagen gelation, a quantity of a gelation inhibitor agent such as urea is added to the aqueous system. By using the gelation inhibitor agent, the deposition of the structural protein and the apatite onto the substrate can occur simultaneously to obtain a homogenous structural protein/apatite nanocomposite coating. For example, when collagen and apatite are deposited in the presence of urea, a nano-composite coating is formed having a structure similar to natural bone.

The coating aqueous system used to prepare the coatings can contain an amount of a gelation inhibitor agent to allow for the controlled deposition of structural protein and apatite onto a substrate. Exemplary gelation inhibitor agents include urea, histidine, hydroxyproline, thiourea, sodium dodecyl sulfate, lithium dodecyl sulfate, 2-mercaptoethanol, formamide, dithiothreitol, CHAPS (3-[(3-cholamidopropyl)-dimethylammonio]-1-propane sulfonate), CHAPSO (3-([cholamidopropyl]-dimethyl ammonio)-2-hydroxy-1-propanesulfonate), guanidinium chloride (guanidine hydrochloride), guanidinium thiocyanate, and the like; specifically urea. The amount of gelation inhibitor agent present in the coating aqueous system can be about 0.1 M to about 6.0 M, specifically about 0.2 M to about 1.0 M, and more specifically about 0.4 M to about 0.6 M.

The structural protein used in the structural protein containing aqueous system can be any known structural protein such as collagens, elastin, and keratins, specifically collagen, and more specifically soluble collagen Types I, II, III, and V, and yet more specifically collagen Type I. As used herein, soluble collagen means "collagen molecules or microfibrils which are soluble in an aqueous solution".

There is no particular limitation as to the source of the structural protein. The structural protein may be obtained from commercial sources or extracted from natural sources using procedures well known in the art.

In one embodiment, a collagen containing coating aqueous system contains about 0.01 to about 0.9 g/L collagen solution, about 5.0 to about 10.0 mM $Ca^{2+}$, about 1.0 to about 5.0 mM $HPO_4^{2-}$, about 100.0 to about 200.0 mM $Na^+$, about 2.0 to about 8.0 mM $K^+$, 1.0 to about 2.0 mM $Mg^{2+}$, 50.0 to about 150.0 mM $Cl^-$, about 5.0 to about 50.0 mM $HCO_3^-$, about 1 to about 1.0 mM $SO_4^{2-}$, about 0.3 to about 0.7 M urea, about 0.1 to about 0.3M acetic acid, and about 5.0 to about 15.0 g/L HEPES.

The density/porosity of the ceramic coating can be adjusted by several parameters including amount of $HCO_3^-$, initial pH of the coating aqueous system, amount of buffer, temperature of the coating process, calcium concentration, phosphate concentration and other ion concentrations (i.e. $Mg^{2+}$).

The density/porosity of the ceramic coating can be adjusted by carefully choosing the initial pH of the coating aqueous system. Over time, the pH of the aqueous system increases due to the bicarbonate ions in the solution naturally decomposing into hydroxyl groups and carbon dioxide. The initial formation of the coating is formed when the aqueous system has an initial pH of about 5.0 to about 8.0. The initial stage of the coating process is slower as $HCO_3^-$ inhibits the crystal growth of the coating. Therefore, the coating will grow slower and denser at the initial stages of the coating process as the concentration $HCO_3^-$ is initially high. As the $HCO_3^-$ ions decompose, the rate of coating formation increases and the inhibitory effect of the bicarbonate ions is less pronounced.

The amount of buffer in the aqueous system will also alter the pH change profile during the coating process. When there is less buffer in the aqueous system, more $HCO_3^-$ will be present in the system when the pH range for apatite formation is achieved.

The calcium and phosphate concentrations can also be chosen to obtain the optimal pH range for apatite formation. Magnesium ions are known to decrease the rate of apatite formation and thereby attributes to the formation of a relatively dense coating.

If needed, the initial pH of the coating aqueous system can be adjusted by the addition of an inorganic acid or inorganic base. An exemplary inorganic acid includes halo acids (e.g. hydrochloric acid). Exemplary inorganic bases include alkali metal hydroxides (e.g. NaOH, KOH, etc.). The initial pH of the aqueous system can be about 5.0 to about 8.0, specifically about 5.8 to about 7.5, more specifically about 6.0 to about 6.60, yet more specifically about 6.10 to about 6.45, and still yet more specifically about 6.20 to about 6.38. As used herein, "initial pH" means the pH of the coating aqueous system prior to contact with the substrate to be coated.

The initial pH of the coating aqueous system and the type and amount of buffer system can be selected to generate a desired ceramic coating. After the desired coating aqueous system is prepared, the substrate is exposed to the coating aqueous system at a particular temperature to allow for the formation of the coating. The substrate can be exposed to the coating aqueous system for a time sufficient for the formation of a coating of sufficient thickness. Coatings having sufficient thickness can be formed in less than about 3 days. Specifically, the substrate can be exposed in the aqueous system for about 1 to about 48 hours, specifically about 10 to about 40 hours, more specifically about 12 to about 35 hours, and yet more specifically about 20 to about 30 hours until the desired thickness of coating is formed.

In a generalized process, substrates to be coated are placed in a 2× volume container containing X volume of coating aqueous system. The container is sealed and coating formation is allowed to proceed for about twenty-four hours at about 40° C. After immersion the substrates were removed, gently washed with de-ionized water and air-dried.

The process allows for the variation of structural protein content that is incorporated into the ceramic/structural protein composite coating. Amounts of structural protein (e.g. collagen) incorporated in the coating can be about 0.01 to about 30 weight percent, specifically about 5 to about 25 weight percent, more specifically about 10 to about 20 weight percent, and yet more specifically about 13 to about 17 weight percent based on the total weight of the coating.

Apatite/collagen composite coatings have been shown to be more effective than apatite coating in improving cell attachment and activity of osteoblast-like cells. In the present methods, the amount of collagen content in the apatite/collagen composite coatings can be optimized through the ability to control the collagen weight percent in the coating. Furthermore, the bonding strength of the apatite/collagen composite coating to the substrate is high.

The bonding strength of the coating can be determined using a modified ASTM C-633 method as provided in Kim H-M, Miyaji F, Kokubo T, Nakamura T. "Bonding strength of bonelike apatite layer to Ti metal substrate." *Journal of Biomedical Materials Research* 1997; 38(2):121-127, which is incorporated herein in its entirety.

The coating methods are performed at low temperatures suitable for temperature sensitive substrates such as polymeric materials and hydrogels. The coating process can be performed at a relatively short amount of time. Furthermore, the methods can be used to coat porous substrates and substrates having complex geometries. Additional embodiments are directed to the ceramic coatings themselves as well as articles prepared from substrates comprising the ceramic coatings. In general, the ceramic/structural protein coating can be prepared by exposing a portion of a substrate to a coating aqueous system comprising inorganic ions and a structural protein such as Type I soluble collagen. The substrate is exposed for a period of time and at a temperature to allow for the formation of the ceramic/structural protein coating on the exposed surface of the substrate. Exposing can include immersion of the substrate or portion of the substrate to the coating aqueous system. The resulting ceramic coating is generally a bone-like apatite, but can also be other types of calcium phosphate. Exemplary calcium phosphate minerals include $Ca_5(PO_4)_{3-x}(OH)_{1-y}(CO_3)_{x+y}$, $Ca_5(PO_4)_3(OH)$, $Ca_3(PO_4)_2$, $CaHPO_4$, $Ca(H_2PO_4)_2$, and the like.

As used herein "exposing a portion of a substrate" means any portion or all of the substrate is exposed to the aqueous system.

The temperature of the coating aqueous system during the coating process can be about 20 to about 100° C., more specifically about 25 to about 80° C., yet more specifically about 35 to about 60° C., and still yet more specifically about 38 to about 45° C. In one embodiment, the temperature of the coating aqueous system can be varied during the coating process. At different temperatures, the optimal pH range for apatite formation will also be different as the rate of $HCO_3^-$ decomposition is affected by temperature. By increasing the temperature, the greater the rate of $HCO_3^-$ decomposition as compared to lower temperatures for same time period.

In another embodiment, the temperature of the collagen containing coating aqueous system during the coating process can be about 20 to about 50° C., the initial pH of about 5.5 to about 8.0, the collagen at about 0.1 g/L to about 5.0 g/L, the urea at about 0.1 M to about 6.0 M, the $HCO_3^-$ at about 10 to about 150 mM, $HPO_4^{2-}$ at about 1 to about 10 mM, $Ca^{2+}$ at about 2.5 to about 15 mM, and HEPES at about 5 g/L to about 80 g/L.

In yet another embodiment, the temperature of the collagen containing coating aqueous system during the coating process can be about 25 to about 50° C., the initial pH is about 5.5 to about 8.0, the collagen at about 0.3 g/L to about 3.0 g/L, the urea at about 0.2 M to about 3.0 M, $HCO_3^-$ at about 20 to about 100 mM, $HPO_4^{2-}$ at about 3 to about 8 mM, $Ca^{2+}$ at about 4 to about 13 mM, and HEPES at about 10 g/L to about 50 g/L.

In yet another embodiment, the temperature of the collagen containing coating aqueous system during the coating process can be about 35 to about 45° C., the initial pH is about 6.38 to about 6.45, the collagen at about 0.5 g/L to about 1.5 g/L, the urea at about 0.3 M to about 1.0 M, $HCO_3^-$ at about 30 to about 40 mM, $HPO_4^{2-}$ at about 2.5 to about 3.5 mM, $Ca^{2+}$ at about 7 to about 9 mM, and HEPES at about 10 g/L to about 14 g/L.

In still yet another embodiment, the temperature of the collagen containing coating aqueous system during the coating process can be about 35 to about 45° C., the initial pH is about 6.00 to about 6.10, the collagen at about 0.7 g/L to about 1.0 g/L, the urea at about 0.4 M to about 0.5 M, $HCO_3^-$ at about 60 to about 80 mM, $HPO_4^{2-}$ at about 4.5 to about 5.5 mM, $Ca^{2+}$ at about 11 to about 13 mM, and HEPES at about 42 g/L to about 45 g/L.

Generally, the longer the substrate is exposed to the coating aqueous system, the thicker the resulting composite coating will be. Coatings having a total thickness of about 0.1 to about 70 micrometers can be formed, specifically about 1 to about 50 micrometers, yet more specifically about 5 to about 40 micrometers, and still yet more specifically about 10 to about 25 micrometers.

Exemplary substrates that can be coated with the described composite coating include implantable medical devices useful in biomedical applications, including orthopedic applications (e.g., joint prostheses) and devices and appliances for orthodontic applications and dental implants. The aqueous system lends itself to the uniform application of a ceramic coating even to substrates having surfaces of complex geometries. Additional applications in the biomedical field include drug/protein delivery devices. In addition, this coating system can also be used to load living cells, coat the surface of tissue engineering scaffold and other soft tissue replacement materials.

The coatings can be used to prepare medical, surgical, reconstructive, orthopedic, orthodontic, prosthodontic, endodontic or dental devices, implants, appliances, or a component thereof (e.g., a screw or other attaching connector, etc.).

The substrates can be made from a wide variety of material types, including metal, ceramic, polymeric materials, silicon, glass, and the like. When used in biomedical applications, the material should be biocompatible. As used herein, "biocompatible" means being biologically compatible in that a toxic, injurious, or immunological response is not produced in living tissue. Suitable material for the substrate includes, for example, titanium, stainless steel, nickel, cobalt, niobium, molybdenum, zirconium, tantalum, chromium, alloys thereof and combinations thereof. Exemplary polymeric material include polylactide (PLA), poly(glycolic acid) (PGA), poly (methyl methacrylate) (PMMA), other biocompatible polymeric material, and the like. Exemplary ceramic materials include alumina, titania, and zirconia, glasses, and calcium phosphates, such as hydroxyapatite and tricalcium phosphate.

Prior to the coating step, the surface of the substrate can be prepared to improve the adhesion of the coating. The substrate can be cleaned or treated to remove any surface contaminants. The metal substrates can be surface treated by sand-blasting, scoring, polishing, and grinding to increase the surface roughness. Alternatively, the metal substrate can undergo chemical surface treatments prior to coating to provide a level of surface roughness. Exemplary chemical treatments for metal substrates include, acid etchings with strong mineral acids, such as hydrofluoric, hydrochloric, sulfuric, nitric and perchloric acids; treatment with strong alkalis, such as sodium hydroxide, potassium hydroxide; treatment with oxidizing agents such as peroxyhalogen acids, hydroxyperoxides, or hydrogen peroxide to form a metal oxide layer. Washing with deionized or purified water can effect removal of surface contaminants due to the surface treatment.

In another embodiment, a method of coating a substrate with a ceramic/structural protein coating comprises exposing a portion of a substrate to a collagen containing coating aqueous system in a closed system, e.g., a sealed container, at a temperature of about 20° C. to about 45° C. to form a ceramic/collagen coating on a surface of the substrate, wherein the collagen containing coating aqueous system comprises water, collagen, urea, $Ca^{2+}$, $Mg^{2+}$, $Na^+$, $K^+$, $Cl^-$, $HPO_4^{2-}$, $HCO_3^-$ and a buffer system, wherein the coating aqueous system has an initial pH of about 5.5 to about 8.0, and wherein the closed system comprises a volume ratio of headspace to aqueous system of about 5 to about 15 at atmospheric pressure.

Although the coatings have been discussed in terms of its application for implantable medical devices, the coatings can be used for a wide variety of uses, such as a drug delivery carrier, for example. The coatings can be useful in hard tissue replacement materials and also soft tissue replacement materials.

As used herein "bioactive" means the ceramic coating can induce bone ingrowth resulting in the formation of a strong bond across the interface between the coating and the natural bone.

In one embodiment, a reactor vessel is used in the coating process. The reactor vessel comprises a liquid-holding container and a gas valve ("pressure valve") to control the rate of release of a gas from the container. The liquid-holding container can be prepared from a non-reactive or inert material such as glass or Teflon™.

The shape of the interior of the liquid-holding container can be a regular shape such as a cube, a cone, a sphere, a cylinder, or the like. Optionally, the shape of the interior of the liquid-holding container can be similar to the shape of the substrate to be coated. In order to have the container with a shape similar to the substrate, the container can be molded to follow the shape of the substrate to be coated.

In one embodiment, the shape of the interior of the liquid-holding container is hemispheric and the substrate is a hip acetabular cap.

The liquid-holding container can optionally have a volume sufficient to allow a ratio of the coating aqueous system volume to the substrate surface area to be about 5 to about 50.

The gas valve is a gas-releasing valve used to control the rate of release of a gas, such as carbon dioxide, from the liquid-holding container. The gas valve can be a manual gas valve, a pressure-responsive gas valve, or an automated gas valve.

Also disclosed herein is a convenient method of preparing dense ceramic/structural protein composite films at the air-solution interface of a structural protein (e.g., soluble collagen) containing concentrated aqueous system. The coating aqueous systems for preparing the ceramic/structural protein composite coatings discussed above can be used to prepare the composite films. Furthermore, similar conditions for the coating process above, with regard to time and temperature, can be used for preparing the apatite/collagen composite film.

The apatite/collagen composite film can be isolated and optionally purified (e.g., by washing with deionized/purified water). As the film homogenously contains structural protein and hydroxyapatite particles, it can be prepared into a powder and used as a filler material or compressed into a variety of shapes for bone repair/fixation. The resulting material will have mimicking properties of allograft materials. Any process known in the art to convert the film to powder (e.g., grinding and the like) can be used.

EXAMPLES

Example 1

Apatite/Collagen Composite Coating

Biomimetic Method

Type I collagen was extracted from rat tail tendon as previously described in W. Zhang, S. S. Liao, F. Z. Cui, *Chem. Mater.* 2003, 15, 3221. The rat tail tendon was soaked in 0.5 M acetic acid for 3-4 days at 4° C. The solution was centrifuged at 10,000 rpm at 4° C. for 15 minutes and filtered with No. 1 filter paper to remove the insoluble components. NaCl (5% wt %) was added to induce precipitation of collagen, and the precipitates were collected by centrifuging at 10,000 rpm for 15 minutes at 4° C. A collagen solution of ~1.5 grams per liter (g/L) was formed. From this solution, dilute collagen solutions were prepared into different concentrations as shown in Table 1. Urea with a concentration of 0.5 M was added to the collagen solution.

A collagen-containing aqueous system was prepared containing 7.5 mM $Ca^{2+}$ and 3.0 mM $HPO_4^{2-}$, 142.0 mM $Na^+$, 5.0 mM $K^+$, 1.5 $Mg^{2+}$, 103.0 mM $Cl^-$, 27.0 mM $HCO_3^-$, 0.5 mM $SO_4^{2-}$, 0.5M Urea, and 0.2M acetic acid; prepared from NaCl, $NaHCO_3$, $Na_2CO_3$, KCl, $K_2HPO_4 \cdot 3H_2O$, $MgCl_2 \cdot H_2O$, 4-(2-hydroxyethyl)-1-piperazineethanesulfonic acid (HEPES) (11.928 g per 1000 mL water), $CaCl_2$, $Na_2SO_4$, Urea, glacial acid, and 5M NaOH (6.5 mL per 1000 mL water). Analytical grade reagents NaCl, $NaHCO_3$, $MgCl_2$, $K_2HPO_4$ and $CaCl_2$ were dissolved into de-ionized water with desired amounts. HEPES was chosen to buffer the solution and the initial pH was adjusted to about 6.00 to about 7.00 using 5M NaOH.

A commercially available titanium plate (McMaster-Carr) was cut into 15×15×1 millimeter (mm) plates. The titanium plates were polished using a series of silicon carbide papers (grade 600-1200), and then rinsed with de-ionized water in an ultrasonic bath. The titanium plates were dried at room temperature overnight. The clean titanium alloy plates were then soaked in 5 M NaOH solution at 60° C. for 1 day. After alkaline treatment, the titanium plates were gently cleaned with de-ionized water. The titanium plates were immersed in 50 milliliters (ml) of the collagen-containing aqueous system in a sealed 100 ml bottle and allowed to form apatite coating. The coating formation process was studied at 40° C. After immersion for 24 hours, the plates were removed from each solution, gently washed with de-ionized water and air-dried for overnight.

The resulting composite coatings were then characterized with thermogravimetric analysis (TGA). The analyses revealed a controllable collagen content composite coating was achieved.

TABLE 1

|  | Coating A | Coating B | Coating C |
|---|---|---|---|
| Collagen in aqueous solution | 1.5 g/L | 0.9 g/L | 0.45 g/L |
| Collagen in composite coating (wt %) | 18% | 11% | 7% |

Example 2

Apatite/Collagen Composite

Biomimetic Method

Type I collagen was extracted from rat tail tendon as previously described W. Zhang, S. S. Liao, F. Z. Cui, *Chem. Mater.* 2003, 15, 3221. The rat tail tendon was soaked in 0.5 M acetic acid for 3-4 days at 4° C. The solution was centrifuged at 10,000 rpm at 4° C. for 15 minutes and filtered with No. 1 filter paper to remove the insoluble components. NaCl (5% wt %) was added to induce precipitation of collagen, and the precipitates were collected by centrifuging at 10,000 rpm for 15 minutes at 4° C. Collagen was then dissolved in 0.5 M acetic acid to form a collagen solution with a concentration of 0.5 mg/ml. Urea with a concentration of 0.5 M was added to the collagen solution. Analytical grade reagents NaCl, $NaHCO_3$, $MgCl_2$, $K_2HPO_4$ and $CaCl_2$ with desired amounts were placed into the collagen solution. HEPES (4-(2-hydroxyethyl)-1-piperazineethanesulfonic acid) was chosen to buffer the so formed collagen-containing aqueous system. The ion concentrations of the aqueous system are listed in Table 2.

TABLE 2

| Ion | Collagen containing-aqueous system (concentration in mM) |
|---|---|
| $Na^+$ | 109.5 |
| $K^+$ | 6.0 |
| $Mg^{2+}$ | 1.5 |
| $Ca^{2+}$ | 7.5 |
| $Cl^-$ | 110.0 |
| $HCO_3^-$ | 17.5 |
| $HPO_4^{2-}$ | 3.0 |
| $SO_4^{2-}$ | 0 |

TABLE 2-continued

| Ion | Collagen containing-aqueous system (concentration in mM) |
|---|---|
| Urea | 500 |
| Collagen | 0.5 g/L |

The collagen-containing aqueous system was stirred for 10 minutes, and its pH was then adjusted to 6.2 using 5 M sodium hydroxide at room temperature.

Collagen-containing aqueous system of 50 ml was added to a sealed 100 ml bottle to prepare apatite/collagen composite. The composite formation was taken place at 40° C. After the solution was aged for 24 hours, the composite was formed at the air/solution interface. The composite was removed from the solution, gently washed with de-ionized water and air-dried.

Figure 1B:
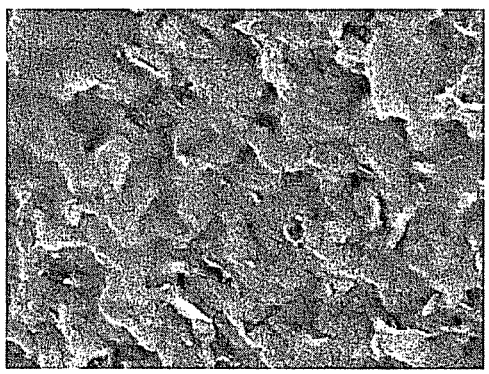
FIG. 1b FESEM image of apatite/collagen composite film surface morphology at a high magnification.
Figure 1C:
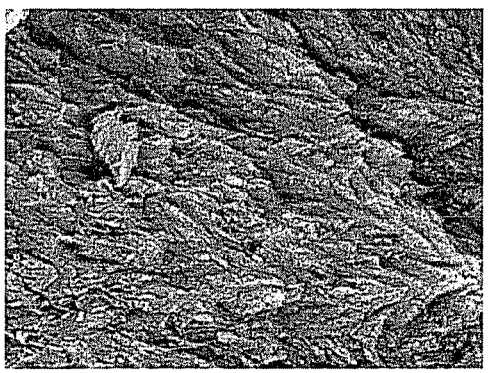
FIG. 1c FESEM image of apatite/collagen composite film cross-section at a high magnification.

The morphology of the composite film was analyzed using a field emission scanning electron microscope (FESEM) (JEOL JSM 6335F). The specimens were coated with gold before FESEM observations. An FESEM image of the composite is shown in FIG. 1a. A higher magnification view (FIG. 1b) shows that the composite is very dense with minimized number of pores at sizes smaller than 100 nanometer (nm). The cross-section morphology of the composite (FIG. 1c) also suggests that the composite is extremely dense, and no pore is observed.

Figure 1D:
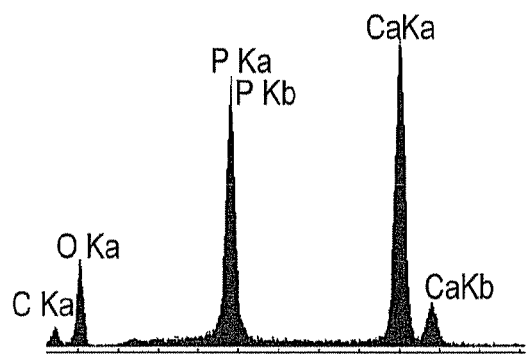
FIG. 1d EDX result of apatite/collagen composite film.

Energy dispersive X-ray (EDX) microanalysis (FIG. 1d) reveals that the composite film is compose of four elements: calcium (Ca), phosphorous (P), oxygen (O), and carbon (C).

The microstructure of apatite/collagen composite film was studied using transmission electron microscopy (TEM). TEM samples were prepared by suspending the composite in an ethanol solution and sonicated for 40 minutes to break up the specimen. A drop of the suspension was then placed onto a copper electron microscope grid. After air-dried, the sample was observed using a JEOL JEM-2010 TEM at 120 kV. The ultra-thin section of the composite was also observed using TEM (FEI Tecnai $G^2$ Biotwin TEM) at 80 kV. The composite film was embedded in Spurr low viscosity epoxy resin (Electron Microscopy Sciences). Ultra-thin sections of the composite were prepared using LKB Ultrotome V ultramicrotomes with diatome diamond knifes, and the sections were transferred onto copper electron microscope grids for TEM observation.

Figure 2A:
FIG. 2a TEM image of the ultra-thin section of apatite/collagen film
Figure 2B:
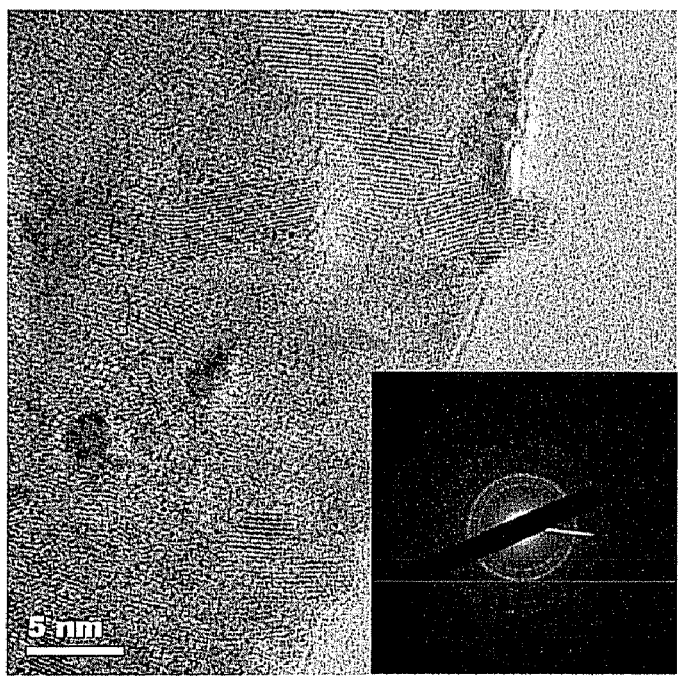
FIG. 2b TEM image and electron diffraction pattern of apatite/collagen composite suspension.

A TEM image (FIG. 2a) shows that the apatite/collagen composite forms into plate-like structure with dimensions around 100 nm×100 nm with thickness about 5 nm (dark line is the cross-section of the plate). FIG. 2b shows the TEM image of nano-sized (around 5 nm in diameter) apatite particles within the composite plate. A typical selected area electron diffraction (SAED) pattern of the composite is also shown in FIG. 2b, where all the rings are attributed to hydroxyapatite (PDF 9-432).

The collagen weight percentage was determined using TGA (TA Instruments TGA Q-500) measurement. The film was heated from room temperature to 800° C. at 10° C./min.

Figure 3:
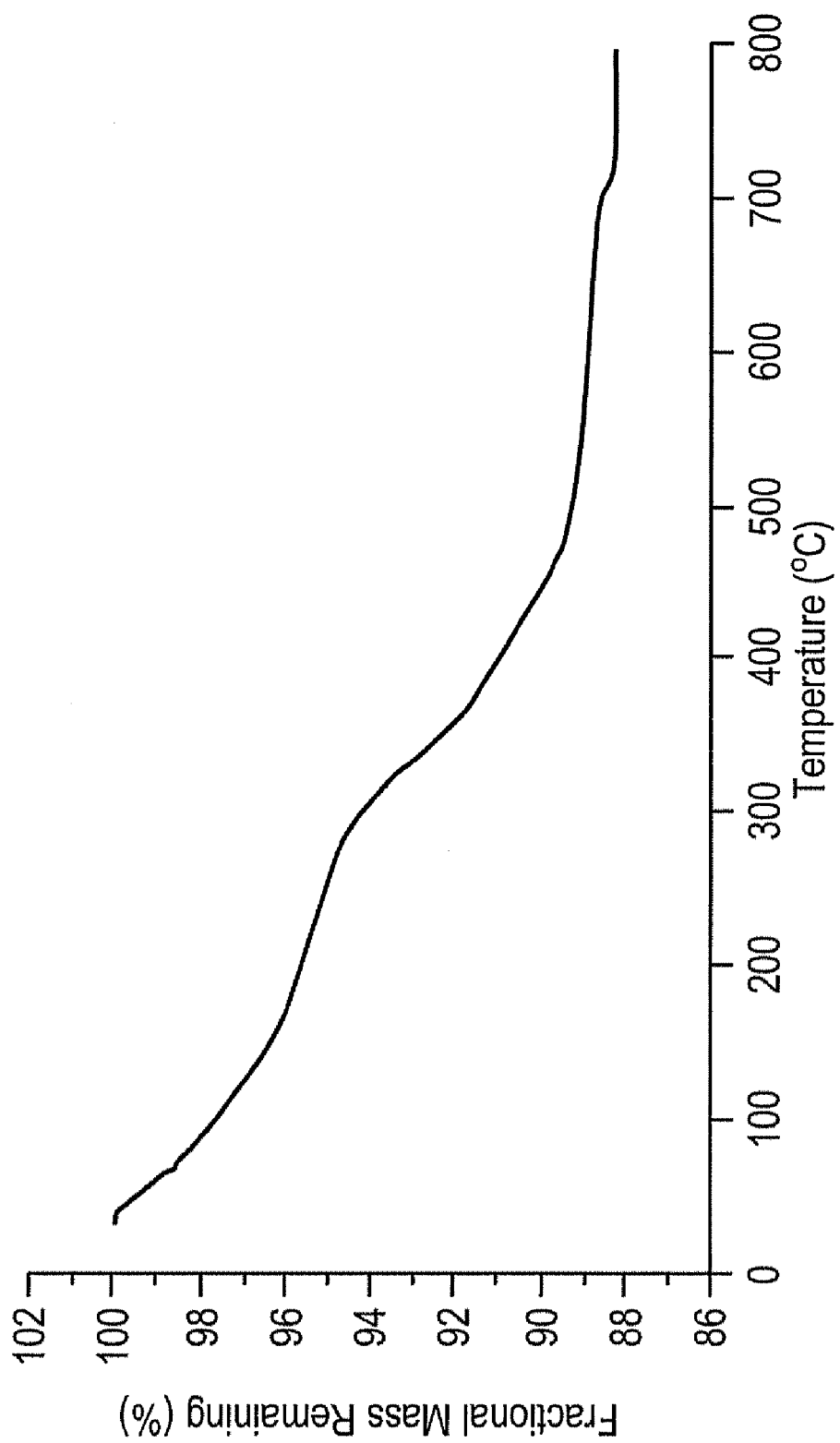
FIG. 3 TGA result of the apatite/collagen composite.

Thermal gravimetric analysis (TGA) profile (FIG. 3) implies that the weight loss of the composite can be divided into three stages. Approximately 6 wt % weight loss occurred at both below 250° C. and within 250-600° C., but only 0.5 wt % weight loss was observed in the temperature range 600 to 800° C. Previous studies suggested that the weight loss in the first stage was mainly associated with water loss, while that in the second stage was attributed to the loss of the organic material (collagen), and then the decomposition of carbonated apatite led to the weight loss in the third stage. The finial remaining product should be pure calcium phosphate. The TGA result revealed that approximately 6 wt % of the composite was made of organic material (collagen).

The as-prepared and heat-treated (after TGA test) composites were grinded into powder and examined using X-ray diffractometer (BRUKER AXS D5005) with a copper target. The voltage and current setup were 40 kV and 40 mA, respectively. A step size of 0.02° and a scan speed of 0.5°/min were used.

The XRD result (FIG. 4a) of the as-prepared composite shows that two broad peaks are present at 26° and 32°. These peaks indicated that nano-sized apatite particles were formed in the composite. This result was consistent with the TEM observation that the apatite particles formed in the composite were in the nanometer range. After the TGA test, both apatite and β-tricalcium phosphate (TCP) co-existed in the composite (FIG. 4b), which suggested that the apatite in the composite had a low decomposition temperature (<800° C.) compared with those prepared by a wet process with a decomposition temperature between 1250-1450° C.

Figure 5A:
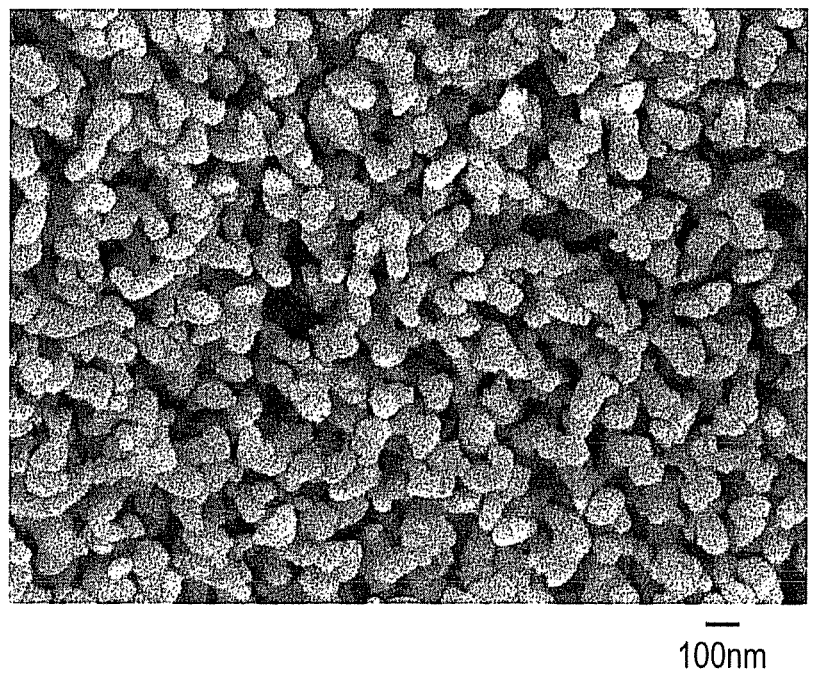
FIG. 5a FESEM image of composite after TGA test.

The morphology of the heat treated (after TGA test) composite films were also evaluated using FESEM. The specimens were coated with gold before FESEM observations. After calcination, all collagen in the composite is burned out leaving pure calcium phosphates. The FESEM image (FIG. 5a) reveals that apatite particles with an average size around 100 nm are closely packed together. The pores among the apatite particles are interconnected with a diameter 100-200 nm. The apatite particles (~100 nm, FIG. 5a) after the TGA test are much larger than those of as prepared (~5 nm, FIG. 2b) due to the growth of apatite particles at high temperatures. The morphologies of the specimens before and after the TGA test were analyzed. Not wishing to be bound by theory, it is believed that the collagen was filled in the voids among apatite particles in the composite before the TGA test.

After soaking in 3% glutaraldehyde solution for 1 hour to crosslink the collagen within the composite, the composite was rinsed with de-ionized water for several times to completely remove glutaraldehyde residues. The composite was then soaked in 0.25 M ethylenediaminetetraacetate (EDTA) solution for 2 hours to dissolve apatite in the composite. The remaining material was carefully collected, rinsed with de-ionized water for several times and air-dried. The specimen was subsequently coated with gold for FESEM observation. The elements in both the as-prepared composite and the remaining material after glutaraldehyde and EDTA treatments were determined using an environmental scanning electron microscopy (ESEM) (ESEM 2020 Philips) equipped with energy-dispersive x-ray (EDX) using an EDAX CDU leap detector system.

Figure 5B:
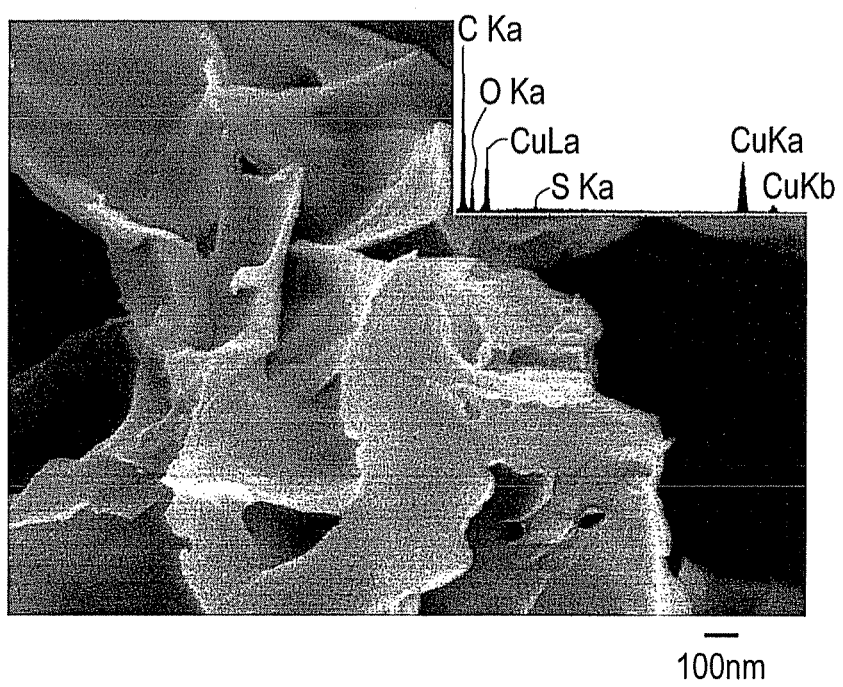
FIG. 5b FESEM image of the composite film after treated with both glutaraldehyde and EDTA.

After treated with glutaraldehyde and EDTA, the collagen in the composite was cross-linked and fixed before the calcium phosphate was removed by EDTA. EDX examination of the treated sample (FIG. 5b) exhibited that only copper (Cu), carbon (C), oxygen (O) and sulfur (S) were present in the specimen, where the copper signal came from the supporting TEM copper grid. The carbon, oxygen and sulfur peaks suggested that only protein remained in the composite after the treatments as it was expected. Compared with the EDX result of the as-prepared composite, it was noted that both calcium and phosphate elements existed in the composite before glutaraldehyde and EDTA treatments. It was also revealed by the FESEM observation (FIG. 5b) that the remaining collagen demonstrated irregular flake shape with dimensions of 200-500 nm×~200 nm×~20 nm.

As shown by this Example, aggregation of apatite nanoparticles and collagen molecules occur simultaneously at the air/water interface to develop an apatite/collagen composite. In the collagen-containing aqueous system, both collagen and apatite could self-assemble into small nuclei when the pH of the solution reached a certain range. Based on the apatite morphology after the TGA test, it is inferred that the apatite particles are evenly distributed among the collagen fibrils. These collagen fibrils and apatite nanoparticles demonstrated a flake-like structure, which then formed into dense apatite/collagen nanocomposites. The apatite/collagen composite formed into a platelet shape with one hundred nanometers in each dimension and less than 10 nm in thickness. The nano-sized apatite (~5 nm) particles were evenly distributed within the composite. These apatite/collagen composite platelets were strongly adhered to each other and formed into dense composite films.

The terms "a" and "an" herein do not denote a limitation of quantity, but rather denote the presence of at least one of the referenced item. The suffix "(s)" as used herein is intended to include both the singular and the plural of the term that it modifies, thereby including one or more of that term (e.g., the metal(s) includes one or more metals). Ranges disclosed herein are inclusive and independently combinable (e.g., ranges of "up to about 25 wt %, or, more specifically, about 5 wt % to about 20 wt %", is inclusive of the endpoints and all intermediate values of the ranges of "about 5 wt % to about 25 wt %," etc).

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method of coating a substrate, comprising:
    exposing a portion of a substrate to an aqueous system at a temperature of about 20° C. to about 80° C. to form a ceramic coating on a surface of the substrate;
    wherein the aqueous system comprises a structural protein, a gelation inhibitor agent, a weak acid having a pKa of about 3.0 to about 5.5, water, $Ca^{2+}$, $HPO_4^{2-}$, a buffer system, and optionally one or more of $Mg^{2+}$, $Na^+$, $K^+$, $Cl^-$, $SO_4^{2-}$; or $HCO_3^-$; and
    wherein the aqueous system has an initial pH of about 5.0 to about 8.0.

2. The method of claim 1, wherein the structural protein is collagen Type I, II, III, or V.

3. The method of claim 1, wherein the gelation inhibitor agent is urea, histidine, hydroxyproline, thiourea, sodium dodecyl sulfate, lithium dodecyl sulfate, 2-mercaptoethanol, formamide, dithiothreitol, (3-[(3-cholamidopropyl)-dimethylammonio]-1-propane sulfonate), (3-([cholamidopropyl]-dimethyl ammonio)-2-hydroxy-1-propanesulfonate), guanidinium chloride (guanidine hydrochloride), or guanidinium thiocyanate.

4. The method of claim 1, wherein the buffer system comprises 4-(2-hydroxyethyl)-1-piperazineethanesulfonic acid, 4-(2-hydroxyethyl)-1-piperazineethanesulfonic acid salts, tris-hydroxymethyl aminomethan, piperazine-1,4-bis(2-ethanesulfonic acid), piperazine-1,4-bis(2-ethanesulfonic acid) salts, or combinations thereof.

5. The method of claim 1, wherein the weak acid is an organic carboxylic acid having a pKa of about 3.0 to about 5.5.

6. The method of claim 1, wherein
    the structural protein is collagen Type I present in an amount of about 0.1 g/L to about 5.0 g/L;
    the gelation inhibitor agent is urea present in an amount of about 0.1 M to about 6.0 M;
    $Ca^{2+}$ is present in an amount of about 2.5 to about 15.0 mM;
    $Mg^{2+}$ is present in an amount of about 0.5 to about 5.0 mM;
    $Na^+$ is present in an amount of about 50.0 to about 300.0 mM;
    $K^+$ is present in an amount of about 2.0 to about 20.0 mM;
    $Cl^-$ is present in an amount of about 50.0 to about 350.0 mM;
    $SO_4^{2-}$ is present in an amount of about 0 to about 2.0 mM;
    $HPO_4^{2-}$ is present in an amount of about 1.0 to about 10.0 mM; and
    $HCO_3^-$ is present in an amount of about 5.0 to about 100.0 mM.

7. The method of claim 1, wherein the exposing the substrate to the aqueous system occurs for a time of about 10 hours to about 48 hours.

8. The method of claim 1, wherein the substrate comprises a metal, a ceramic, a polymeric material, or silicon.

9. The method of claim 1, wherein the coating is performed in a sealed container, wherein the sealed container comprises a pressure valve.

* * * * *